(12) United States Patent
Schreiber et al.

(10) Patent No.: US 8,872,133 B2
(45) Date of Patent: Oct. 28, 2014

(54) DEVICE FOR MEASURING THE FLUORESCENCE OF A MEDIUM

(75) Inventors: Marco Schreiber, Duisburg (DE); Thomas Fritsch, Mönchengladbach (DE)

(73) Assignee: KROHNE Optosens GmbH, Neuss (DE)

( * ) Notice: Subject to any disclaimer, the term of this patent is extended or adjusted under 35 U.S.C. 154(b) by 395 days.

(21) Appl. No.: 12/775,855

(22) Filed: May 7, 2010

(65) Prior Publication Data

US 2010/0282982 A1    Nov. 11, 2010

(30) Foreign Application Priority Data

May 7, 2009 (DE) .......................... 10 2009 020 252

(51) Int. Cl.
  *G01J 5/58* (2006.01)
  *G01N 21/64* (2006.01)
  *G01N 21/85* (2006.01)
  *G01N 21/53* (2006.01)

(52) U.S. Cl.
  CPC ............ *G01N 21/6486* (2013.01); *G01N 21/85* (2013.01); *G01N 2201/1211* (2013.01); *G01N 2021/6491* (2013.01); *G01N 21/53* (2013.01)
  USPC .................................................... 250/459.1

(58) Field of Classification Search
  USPC .................................................... 250/459.1
  See application file for complete search history.

(56) References Cited

U.S. PATENT DOCUMENTS 4,558,014 A * 12/1985 Hirschfeld et al. ............ 436/527
4,750,837 A *  6/1988 Gifford et al. ................. 356/417
5,094,819 A *  3/1992 Yager et al. ................. 422/82.07

(Continued)

FOREIGN PATENT DOCUMENTS

DE   199 34 934 C1   6/2001
DE   100 02 238 A1   7/2001
EP   1 918 385 A1   5/2008

OTHER PUBLICATIONS

David F. Eaton, "Reference Materials for Fluorescence Measurement", Pure and Appl. Chem., vol. 60, No. 7, pp. 1107-1114, 1988.*

(Continued)

*Primary Examiner* — David Porta
*Assistant Examiner* — Edwin Gunberg
(74) *Attorney, Agent, or Firm* — Roberts Mlotkowski Safran & Cole, P.C.; David S. Safran

(57) ABSTRACT

A device for measuring the fluorescence of a medium having a radiation source, an emission-receiving element and an optical imaging element arranged on the sensor side of the optical imaging element, and a scattering-receiving element arranged on the sensor side of the optical imaging element and in which the radiation source, the imaging element and the emission-receiving element are aligned and configured relative to one another so that the medium present on the medium side of the imaging element can be illuminated by radiation from the radiation source, and the emission intensity of the medium radiation emitted by the medium based on fluorescence can be detected with the emission-receiving element. To provide a device for measuring the fluorescence of a medium which has an increased reliability in measuring the fluorescence, temperature compensation is performed relative to the temperature of the medium and/or at least one of the receiving elements.

6 Claims, 6 Drawing Sheets

(56) References Cited

U.S. PATENT DOCUMENTS

| | | | |
|---|---|---|---|
| 6,124,937 A | 9/2000 | Mittenzwey et al. | |
| 6,505,059 B1 * | 1/2003 | Kollias et al. | 600/316 |
| 7,151,604 B2 | 12/2006 | Saccomanno et al. | |
| 7,256,883 B2 | 8/2007 | Detinkin et al. | |
| 7,319,522 B2 | 1/2008 | Havard et al. | |
| 7,372,038 B2 * | 5/2008 | Hassard et al. | 250/372 |
| 7,420,679 B2 | 9/2008 | Treado et al. | |
| 7,436,501 B2 | 10/2008 | Hashimoto et al. | |
| 7,474,400 B2 | 1/2009 | Tartakovsky et al. | |
| 7,532,320 B2 | 5/2009 | Neiss et al. | |
| 7,558,619 B2 | 7/2009 | Ferguson et al. | |
| 7,596,253 B2 | 9/2009 | Wong et al. | |
| 7,697,576 B2 | 4/2010 | Maier et al. | |
| 7,923,801 B2 * | 4/2011 | Tian et al. | 257/440 |
| 7,990,525 B2 | 8/2011 | Kanda | |
| 2005/0233388 A1 | 10/2005 | Anderson | |
| 2006/0124443 A1 | 6/2006 | Tuschel et al. | |
| 2006/0247537 A1 | 11/2006 | Matsumoto | |
| 2007/0178067 A1 | 8/2007 | Maier et al. | |
| 2008/0027280 A1 | 1/2008 | Fengler et al. | |
| 2008/0102473 A1 | 5/2008 | Fouquet et al. | |
| 2008/0175790 A1 | 7/2008 | Sevick-Muraca et al. | |
| 2008/0234984 A1 | 9/2008 | Ortyn et al. | |
| 2008/0317325 A1 | 12/2008 | Ortyn et al. | |
| 2009/0137908 A1 | 5/2009 | Patwardhan | |
| 2009/0236541 A1 | 9/2009 | Lomnes et al. | |
| 2011/0036995 A1 * | 2/2011 | Binnie et al. | 250/459.1 |

OTHER PUBLICATIONS

Asylbek Kulmyrzaev et al., "Determination of lactulose and furosine in milk using front-face fluorescence spectroscopy", Lait 82, 725-732 (2002).*

* cited by examiner

DEVICE FOR MEASURING THE FLUORESCENCE OF A MEDIUM

BACKGROUND OF THE INVENTION

1. Field of the Invention

The invention relates to a device for measuring the fluorescence of a medium having at least one radiation source, at least one emission-receiving element and at least one optical imaging element, wherein the radiation source and the emission-receiving element are arranged on the sensor side of the optical imaging element and wherein the radiation source, the imaging element and the emission-receiving element are aligned and designed in respect to one another so that the medium present on the medium side of the imaging element can be illuminated by radiation from the radiation source and the emission intensity of the medium radiation emitted by the medium based on fluorescence can be detected with the emission-receiving element, wherein at least one scattering-receiving element is arranged and designed on the sensor side of the optical imaging element so that the scattering intensity of the medium radiation scattered by the medium in the range of the absorption of the radiation of the radiation source caused by the fluorescence of interest can be detected with the scattering-receiving element.

2. Description of Related Art

Measuring devices of this type have been known for a long time and are used, for example, in the fields of chemical analysis and in environmental and quality control. Such devices use the fluorescence of particles of the medium—fluorophores—i.e., the short-term emission of light from fluorphores caused by suitable spectral electromagnetic excitation. Radiant energy is absorbed by the fluorophores and—partially—re-released by emission of light based on fluorescence, wherein the emitted light has a characteristic spectrum, i.e., radiant energy is only emitted at certain frequencies. The emission intensities of the medium radiation emitted based on fluorescence detected by the emission-receiving device, thus allows, for example, a conclusion about the concentration of the fluorescent particles of interest within the medium.

The extent of the emission intensity detected by the emission-receiving element, i.e., the medium radiation emitted from the medium based on fluorescence, depends—as in many real technical measuring devices—on the constructive design of the measuring device, for example on the arrangement of the emission-receiving element, the medium and the radiation source in relation to one another, so that it is to be taken into account that the part of the medium radiation emitted based on fluorescence, which is detected by the emission-receiving element, allows a reliable conclusion about the entire emission intensity. Naturally, such a measurement is afflicted with some uncertainty.

SUMMARY OF THE INVENTION

The primary object of the present invention is to provide a device for measuring the fluorescence of a medium, in which the above-mentioned disadvantages—at least partially—are avoided, which has, in particular, an increased reliability in measuring the fluorescence of a medium.

The above object is met according to the invention initially and essentially with the device being discussed here in that a compensation occurs in respect to the temperature of the medium and/or in respect to the temperature of at least one of the receiving elements. This compensation allows for a particularly large accuracy and reliability to be achieved in measuring the fluorescence of a medium according to the invention. The compensation of temperature is successful due to the temperature of the medium or the temperature of the receiving element to be compensated in respect to temperature being initially detected using metrology. The effective temperature is then used in that a known correlation between the medium temperature and the fluorescence of the medium or the temperature of the respective receiving element and its sensitivity during evaluation of the measuring signal are taken into account. The "known correlation" can, of course, be initially determined in upstream test runs. It is first possible with the measure according to the invention to carry out actual qualitatively and also quantitatively reliable measurements of the fluorescence, since an essential influencing factor is taken into account, an influencing factor that is relevant in two ways, namely in respect to the intensity of the fluorescence and thus the generation of the measuring signal—assuming continuous excitation—as well as in respect to the detection of the radiation based on fluorescence by the receiving element.

The aforementioned device for measuring the fluorescence of a medium takes advantage according to the invention of the knowledge that the radiant energy emitted from the medium through fluorescence must have been previously removed—i.e., absorbed—from the radiation of the radiation source by the fluorescent parts of the medium, so that the change in the scattering intensity of the medium radiation scattered from the medium in the frequency range, in which the fluorescence of interest is excited, behaves inversely proportionally to the change of the emission intensity of the medium radiation emitted from the medium by fluorescence.

Using the detection according to the invention of a second variable coupled functionally to the fluorescence, it is possible to make a reliable conclusion about the fluorescence of interest or about the characteristics coupled functionally to the appearance of fluorescence, as, for example, the concentration of the fluorescent particles within the medium.

In an advantageous design of the measuring device according to the invention, it is provided that a beam splitter is arranged between the radiation source and the imaging element and the beam splitter guides a known portion of the radiation emitted from the radiation source—in the following referred to as reference radiation—to the reference receiving element and the reference radiation can be detected by the reference receiving element, which also allows for the source intensity of the radiation source to fundamentally be detected by the reference receiving element. This design has the advantage that the device can be internally calibrated in respect to the source intensity of the radiation source, so that changes due to external influences or changes due to aging of the source intensity of the radiation can always be taken into account. Here, the beam splitter and the reference receiving device are preferably aligned so that reflection of the medium cannot reach the reference receiving element, which would falsify the detection of the source intensity of the radiation source.

In order to avoid the detection of reflection from the medium, the reference receiving element is preferably oriented so that the reference receiving element is either oriented more in the direction of the radiation source than in the direction of the medium or the reference receiving element is arranged close to the radiation source so that a reflection from the medium is already avoided due to the spacing from the medium.

The term "beam splitter" is to be understood in such a manner that not necessarily the portion of the radiation of the radiation source, which is struck by the beam splitter, has to be split into multiple beams, but in the manner that a portion of the radiation of the radiation source—the reference radiation—is deflected in the direction of the reference receiving element. All in all, such splitting of the total radiation of the radiation source is achieved, wherein the entire source radiation does not have to run through the beam splitter.

According to a further advantageous design of the invention, the device according to the invention has an evaluating unit for calculating the fluorescence of the medium, wherein in addition to the emission intensity of the medium radiation emitted by the medium using fluorescence detected by the emission-receiving element, also the scattering intensity of the medium radiation scattered by the medium in the range of the absorption caused by the fluorescence of interest and detected by the scattering-receiving device is conveyed to the evaluation unit. Additionally or alternatively, the source intensity of the radiation source detected by the reference receiving element is also conveyed to the evaluation unit. This is advantageous in particular in view of a further preferred design of the invention, according to which the evaluation unit converts the detected emission intensity of the medium radiation emitted based on fluorescence in combination with, behaving inversely proportional to the emission intensity, the scattering intensity of the medium radiation scattered by the medium in the range of the absorption of the radiation of the radiation source caused by the fluorescence of interest into a concentration value of the fluorescent parts of the medium, in particular after calibration with the source intensity of the radiation source detected by the reference receiving element. For this reason, the device for measuring the fluorescence can be tuned for very specific tasks, for example, not only can concentration values of the fluorescent molecular components of the medium be given, but also concentrations from larger units of the medium, which, in turn, contain the fluorescent components.

For very specific measurement of fluorescence of a medium, i.e., in exclusive measurement of a certain characteristic of absorption and emission bands, it has been shown to be advantageous and practical when a source-side optical filter having bandpass characteristics is arranged between the radiation source and the imaging element or between the radiation source the beam splitter in the device according to the invention, wherein the source-side optical filter is maximally permeable for the frequency range of the radiation of the radiation source with which the fluorescence of interest of the medium can or should be excited. This measure allows that, on the one hand, a fluorescence of the medium is only very selectively excited at a certain frequency of the radiation of the radiation source and multiple fluorescent components of the medium are not excited using broad-band excitation, so that, on the other hand, only a few different frequencies are present and observable at all on the receiving side in the medium radiation. Due to the source-side optical filter, the application of the device for measuring the fluorescence of a medium is limited, but it simplifies the construction of the receiving and evaluating side of the device.

According to a further advantageous design of the invention, it is provided that an optical emission filter having bandpass characteristics is arranged between the imaging element and the emission-receiving element, wherein the optical emission filter is maximally permeable for the frequency range of the medium radiation in which the radiation of the medium of interest excited by fluorescence lies. The optical emission filter is normally an interference filter, with which a low full width at half maximum and low transmission in the stop band can be achieved. Even when the medium is excited broad-band on the source side, a very simple evaluation of the medium radiation in the range of the fluorescence frequency of interest can be achieved using the optical emission filter.

Taking this into consideration, a further advantageous design of the device according to the invention is characterized in that an optical scattering filter having bandpass characteristics is arranged between the imaging element and the scattering-receiving element, wherein the optical scattering filter is maximally permeable in the frequency range of the medium radiation in which the medium has its absorption maximum caused by the fluorescence of interest. The advantage is achieved that all frequency ranges of the medium radiation that do not lie in the range of the absorption maximum can be hidden, so that only the evaluation of the radiation suitable for the absorption band even reach the scattering-receiving element.

According to a further advantageous design of the invention, it is provided that at least one of the receiving elements is a photo multiplier. Photo multipliers provide a considerably improved sensitivity as opposed to the use of cameras or photo diodes, in particular in the UV range.

A further, independent teaching of the invention consists of a method for the purpose of fluorescent spectroscopic in-line determination of the protein content of a medium containing milk, which includes: a step for measuring the fluorescence of the medium using the device described above according to the invention.

The advantage of the described method for the purpose of fluorescent spectroscopic in-line determination of the protein content of a medium containing milk is especially seen in consideration of the currently established methods, which are not suitable for in-line determination of the protein content since they normally are based on taking a sample from the observed process.

A reference method for determining the protein content in the milk industry is the wet chemistry Kjeldahl method, in which the milk sample is made soluble with sulfuric acid and then ammonia is liberated with sodium hydroxide, which is then titrated after adding boric acid; an in-line measurement—i.e., a measurement in the process, e.g., in the reactor or in the material flow—is not possible here, a part of the product ultimately has to be channeled off. The same also holds true for the method according to Dumas, which is also a wet chemistry method, in which the sample taken can no longer be used for the further process.

Dairies nowadays also use infrared technology for intake and process controls of the protein content in which the relatively selective amide absorption bands are measured in the NIR and MWIR ranges (NIR=near infrared; MWIR=midwave infrared). The measuring devices used for this, however have to be recurringly calibrated with the results of a reference analysis—e.g according to Kjeldahl.

The method according to the invention and the respective device, as opposed to the method described above, are suitable for the in-line measurement of the protein content of a medium containing milk, since a continuous calibration using sampling is not necessary.

According to the invention, it has been seen that transmission of the NIR spectroscopy onto the determination of the protein content of a medium containing milk is not easily possible, since extreme superimposition of overtones of different oscillation states of the milk content occurs in the wave range of the near infrared and, thus, none of the bands correlate specifically with the content of protein. Furthermore, the bands are superimposed with dominating water absorption and the measuring signal is impaired by scattering in particles with unknown particle size distribution.

According to the invention, it has been further recognized that measuring fluorescence as a method for determining the protein content via the measurement of the emission intensity of the medium radiation emitted by the medium through fluorescence and by measuring the scattering intensity of the medium radiation scattered by the medium in the range of the absorption caused by the fluorescence of interest is particularly suitable since a comparably long wavelength shift of the emission wavelength compared to the absorption wavelength occurs and it is, thus, particularly simple to detect the radiation used to excite the fluorescence completely separated from the radiation emitted through the fluorophore. The detected radiation thus contains, in the best case, only information about the fluorescent components of the medium containing milk, whose protein content is to be determined.

Furthermore, the method according to the invention is advantageous because milk contains, in total, a manageable amount of fluorescent components, whose absorption characteristics—as opposed to in the NIR range—are only slightly impaired in the wavelength range suitable for measuring fluorescence.

Furthermore, the combination of absorption and emission wavelengths for the respective fluorophore—in the respective surroundings—is characteristic, so that the relative band position of the absorption and emission band can be used for detection. Furthermore, the method is non-destructive and independent of the optical density of the medium.

The method according to the invention can be carried out particularly advantageously when the fluorescence of tryptophan is used for the determination of the protein content of the medium containing milk. Here, it has been seen and taken into consideration that the maximum absorption of tryptophan is found in a relatively short-waved range of the electromagnetic light spectrum, while other contents absorb longer waved or shorter waved electromagnetic radiation which is why there is only little disturbance. Furthermore, tryptophan has a comparably high molar extinction coefficient, i.e., it absorbs quite a bit of electromagnetic radiation. All in all, the sensitivity of tryptophan, which is given in general by the product of molar absorptivity and quantum yield, is considerably higher than with other fluorescent alpha amino acids, which makes tryptophan particularly well suited for in-line determination of the protein content of media containing milk.

A measuring device, which is targeted especially for the latter method, is characterized in particular in that the radiation source emits light with a radiation maximum at essentially 289 nm and/or that the source-side optical filter is a bandpass with a maximum permeability at essentially 289 nm and/or that the optical emission filter is a bandpass with a maximum permeability at essentially 340 nm, in particular having a full width at half maximum of 10 nm at the most and/or that the optical scattering filter is a bandpass with a maximum permeability at essentially 289 nm, in particular with a full width at half maximum of 10 nm at the most; this takes into consideration special emission and absorption bands of tryptophan.

In detail, there is a plurality of possibilities for designing and further developing the device according to the invention. Here, please refer, on the one hand, to the patent claims subordinate to patent claims 1 and 10 and to the following description of embodiments in connection with the drawing. The drawing shows:

DETAILED DESCRIPTION OF THE INVENTION

Figure 1:
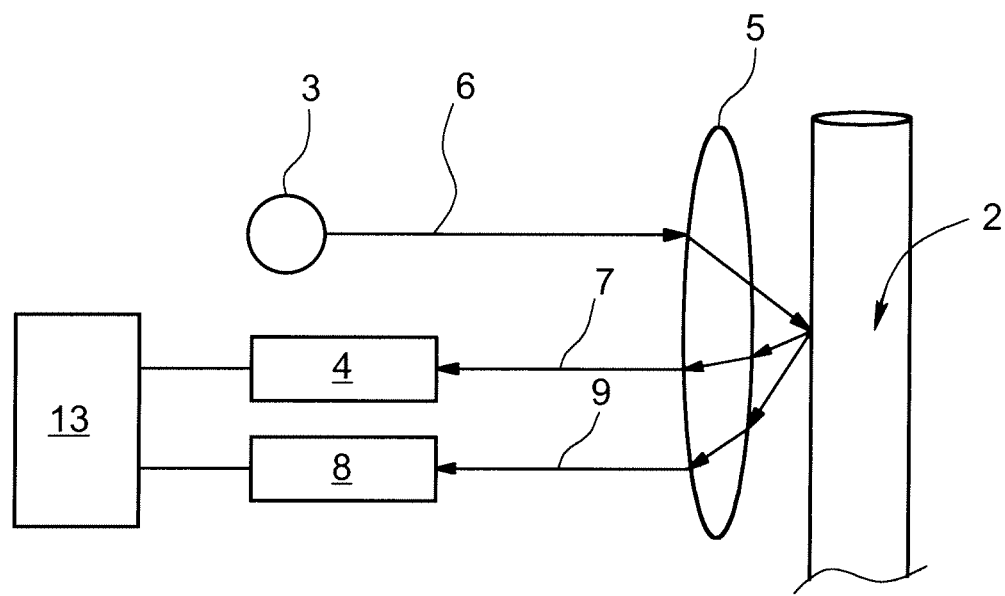
FIG. 1 schematically shows a first embodiment of a device for measuring the fluorescence of a medium, FIG. 2 schematically shows a modified embodiment of a device according to the invention for measuring the fluorescence of a medium, FIG. 3 schematically shows a another modified embodiment of a device according to the invention for measuring the fluorescence of a medium.

In FIGS. 1 to 6, the devices 1, or sections of devices 1, for measuring the fluorescence of a medium 2 are shown having a radiation source 3, an emission-receiving element 4 and an optical imaging element 5, wherein the radiation source 3 and the emission-receiving element 4 are arranged on the sensor side of the of the optical imaging element 5 and wherein the radiation source 3, the imaging element 5 and the emission-receiving element 4 are aligned and designed in respect to one another so that the medium present on the medium side of the imaging element 5 can be illuminated by radiation from the radiation source 3 and the emission intensity of the medium radiation 7 emitted by the medium 2 using fluorescence can be detected.

The shown devices 1 for measuring the fluorescence of a medium 2 are characterized in general in that a scattering-receiving element 8 is arranged and designed on the sensor side of the optical imaging element 5 that the scattering intensity of the medium radiation 9 scattered by the medium 2 in the range of the absorption of the radiation 6 of the radiation source 3 caused by the fluorescence of interest can be detected by the scattering-receiving element 8. This additional detection of the scattering intensity of the medium radiation 9 scattered by the medium 2 is suitable as an additional variable for determining the fluorescence of the medium 2, which is why the determination of the fluorescence of the medium 2 is possible with increased accuracy and increased safety.

Furthermore, a first temperature sensor 30 is provided, which detects the temperature of the medium 2, wherein the measuring signal of the temperature sensor 30 is transmitted to the evaluating unit 13 and the measurement of fluorescence of the medium 2 in respect to the temperature of the medium 2 is compensated in the evaluating unit 13. In addition, the correlation between fluorescence of the medium 2 and temperature of the medium 2 is deposited in the evaluating unit 13 so that compensation of the temperature influence using the present temperature of the medium is possible.

In order to compensate the temperature dependency of the receiving elements 4, 8, the temperatures of these receiving elements 4, 8 are also detected with temperature sensors 31, 32 and made available to the evaluating unit 13. In other embodiments, not shown here, temperature compensation of the receiving elements 4, 8 already occurs in the receiving elements 4, 8 so that temperature-compensated measuring signals are conveyed to the evaluating unit 13.

The embodiment according to FIG. 2 has a beam splitter 10 between the radiation source 3 and the imaging element 5, wherein the beam splitter 10 guides a known part of the radiation 6 emitted by the radiation source 3, which is referred to as reference radiation 11 in the following, to the reference receiving element 12, wherein the reference radiation 11 can be detected by the reference receiving element 12. This means that the source intensity of the radiation source 3 can also be detected by the reference receiving element 12. This allows for changes of the source intensity of the radiation source 3—regardless of how they are caused—to be immediately taken into consideration in the device 1 itself, it could be that the source intensity is given further to an external evaluating unit as separate signal or that, as shown in FIGS. 1 to 3, 5 and 6, a signal corresponding to the detected source intensity of the radiation source 3 is given further to an internal evaluating unit 13 for calculating the fluorescence of the medium 2.

In the embodiment according to FIG. 1, in addition to the emission intensity of the medium radiation 7 emitted by the medium 2 based on fluorescence detected by the emission-receiving element 4, also the scattering intensity of the medium radiation 9 scattered by the medium 2 in the range of the absorption of the radiation 6 of the radiation source 3 caused by the fluorescence of interest and detected by the scattering-receiving element 8 is conveyed to the evaluation unit 13. In the embodiments of the measuring device 1 according to FIGS. 2 and 3, the source intensity of the radiation source 3 detected by the reference receiving element 12 is additionally conveyed to the evaluating unit 13.

The evaluating unit 13 receives other information, for example, about process parameters, which could be of importance for measuring fluorescence or evaluating the measured fluorescence. However, this is irrelevant for understanding the device being discussed her, which is why the availability of "further information" is presently not shown in detail.

Figure 2:
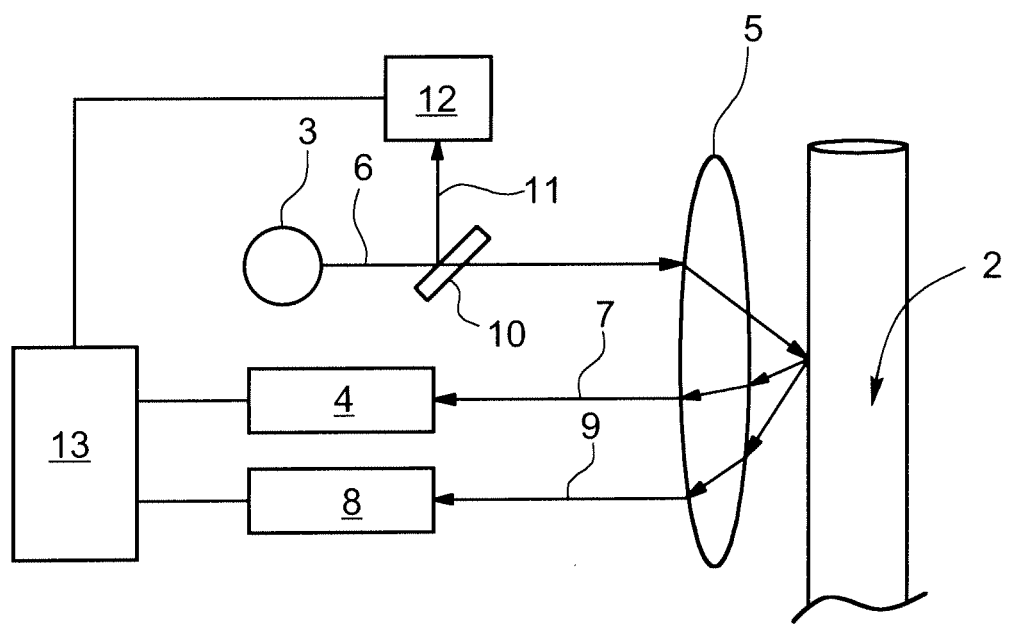
Figure 3:
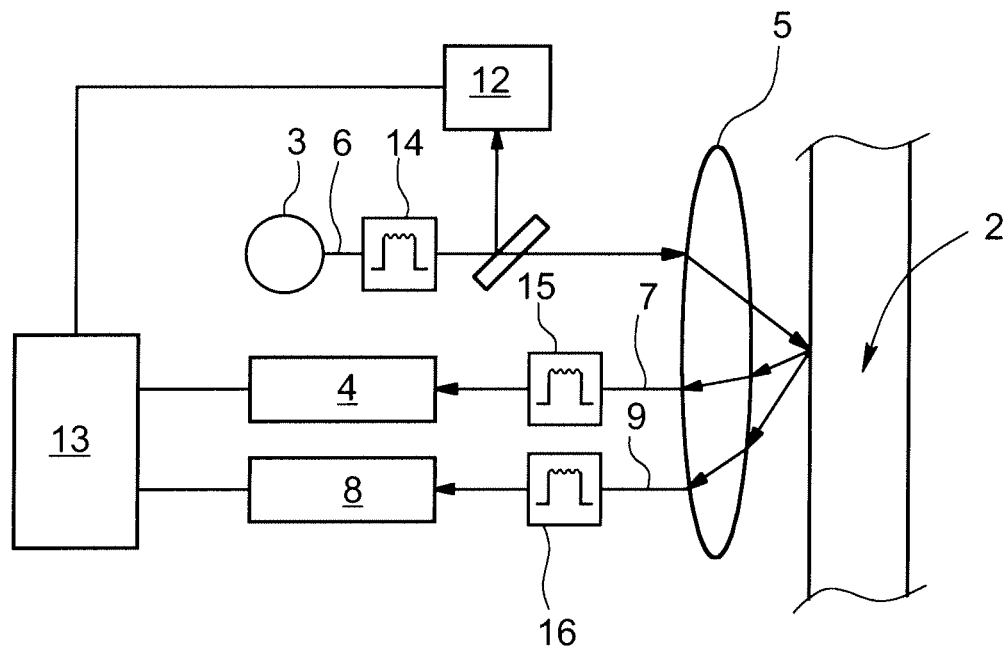

All of the embodiments shown in the figures are characterized in that the evaluating unit 13 converts the detected emission intensity of the medium radiation 7 emitted based on fluorescence in combination with, behaving inversely proportional to the emission intensity, the scattering intensity of the medium radiation 9 scattered by the medium 2 in the range of the absorption of the radiation 6 of the radiation source 3 caused by the fluorescence of interest into a concentration value of the fluorescent particles of the medium 2, which in the embodiments according to FIGS. 2 and 3 occurs after calibration with the source intensity of the radiation source 3 detected by the reference receiving element 12. The device 1 according to FIGS. 2, 3, 5 and 6 are, thus, able to calibrate themselves and do not have to be regularly calibrated—for example, by evaluating samples. For this reason, the evaluating unit 13 is naturally also able to determine the concentration values of other components of the medium, in which fluorescent components are contained in known portions.

For compensating temperature influences, the reference receiving element 12 is provided with a temperature sensor 33, whose measuring signal is also conveyed to the evaluating unit 13, as has been previously described using temperature sensors 30 to 32.

It can be seen in the embodiment according to FIG. 3 that a source-side optical filter 14 having bandpass characteristics is arranged between the radiation source 3 and the beam splitter 10, wherein the source-side optical filter 14 is maximally permeable for the frequency range of the radiation 6 of the radiation source 3 with which the fluorescence of interest of the medium 2 can be excited. This has the advantage that the medium 2 is only very selectively excited and also naturally only a very limited spectrum is present on the receiving side, which can be evaluated more easily and with less disturbance.

For further simplification of the evaluation an optical emission filter 15 having bandpass characteristics is arranged between the imaging element 5 and the emission-receiving element 4, wherein the optical emission filter 15 is maximally permeable for the frequency range of the medium radiation 7 in which the radiation 7 of the medium 2 of interest excited by fluorescence lies. For this reason, only a certain band of the fluorescence of interest can be selectively, reliably evaluated.

Furthermore, an optical scattering filter 16 having bandpass characteristics is arranged between the imaging element 5 and the scattering-receiving element 8 in the device 1 according to FIG. 3, wherein the optical scattering filter 16 is maximally permeable in the frequency range of the medium radiation in which the medium 2 has its absorption maximum caused by the fluorescence of interest. The source-side optical filter 14 and the optical scattering filter 16 are designed similarly since the medium 2 is illuminated with electromagnetic radiation of the frequency in which the absorption maximum is present, since a large part of the radiant energy is re-emitted here by emission based on fluorescence.

Figure 4A:
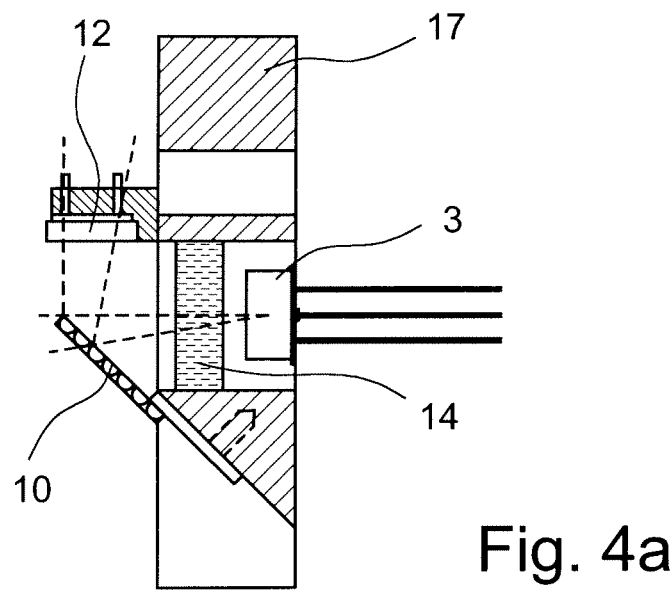
FIG. 4a is a cross sectional view of a support element of a measuring device and FIG. 4b is a plan view thereof.
Figure 4B:
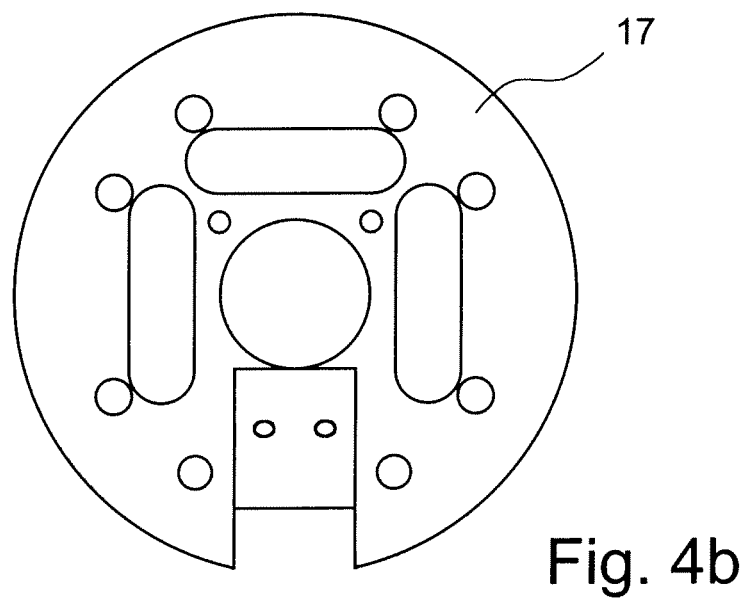

FIG. 4a shows a first holding device 17, in a sectional side view, on which the radiation source 3, the beam splitter 10 and the reference receiving device 12 are commonly arranged; FIG. 4b shows only the first holding device 17. Furthermore, the source-side optical filter 14 is arranged additionally beam-side on the first holding device 17. The beam splitter 10 partially extends into the radiation path of the radiation source 3 and guides a certain portion of the radiation emitted by the radiation source 3, the reference radiation 11, to the reference receiving element 12. The beam splitter 10 and the reference receiving element 12 are arranged in such a manner that no reflection of the medium 2 can be detected by the reference receiving element 12. Presently, the beam splitter 10 is fixed in a recess of the holding device 17, wherein the beam splitter 10 is arranged essentially at a 45° angle to the main direction of radiation of the radiation source 3, so that the main receiving direction of the reference receiving element 12 and the main direction of radiation of the radiation source 3 are essentially at a 90° angle to one another. The holding device 17 is presently integrally formed and provides the advantage of modular summation of all source-side, beam-forming elements, on which the arrangement to one another depends. The radiation source 3 is formed here using an LED (light emitting diode), which emits in narrow band. In other embodiments, not shown here, an optical fiber or a bundle of optical fibers is also part of the radiation source 3, wherein then, only the emitting end of the radiation source is arranged on and attached to the first holding device.

Figure 5:
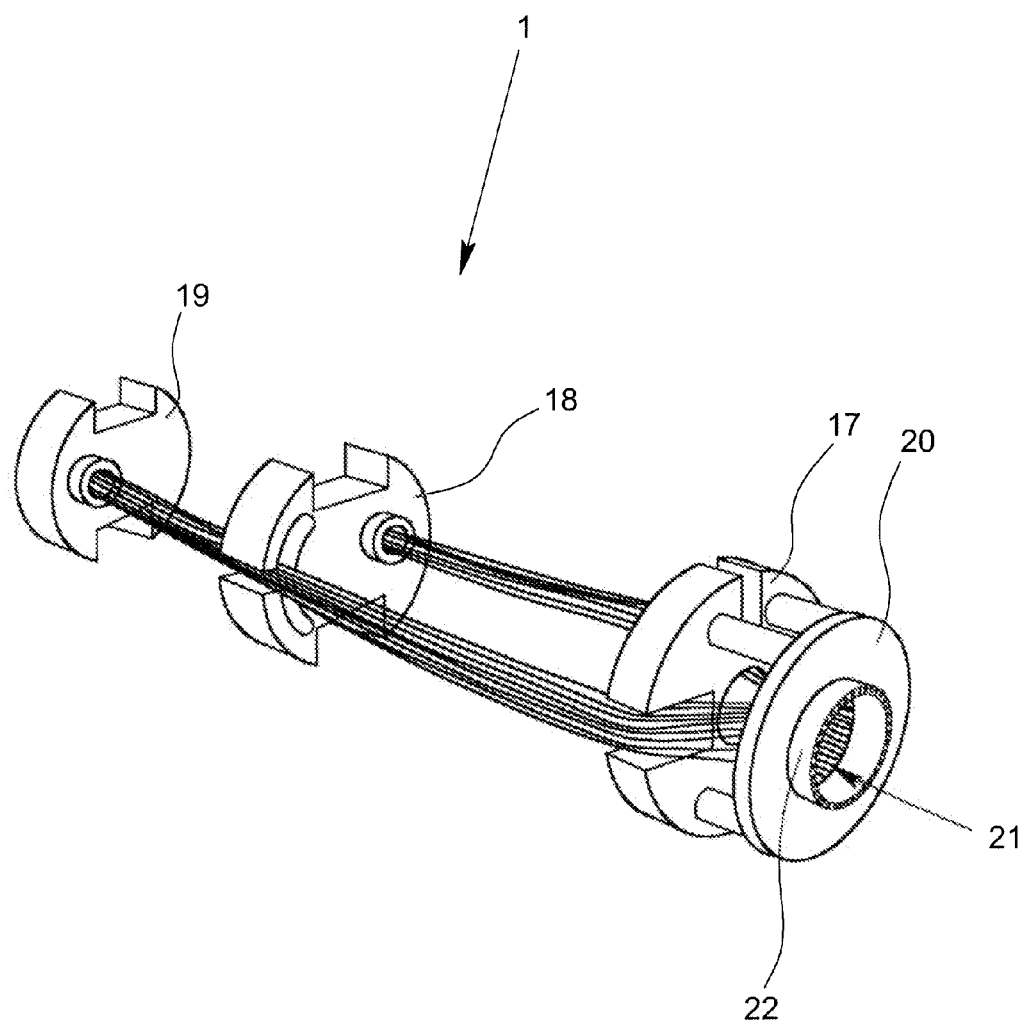
FIG. 5 is a perspective view of an embodiment of a measuring device with support elements arranged flush to one another and FIG. 6 is a perspective view of the embodiment according to FIG. 5 with support elements being held in a holding device.
Figure 6:
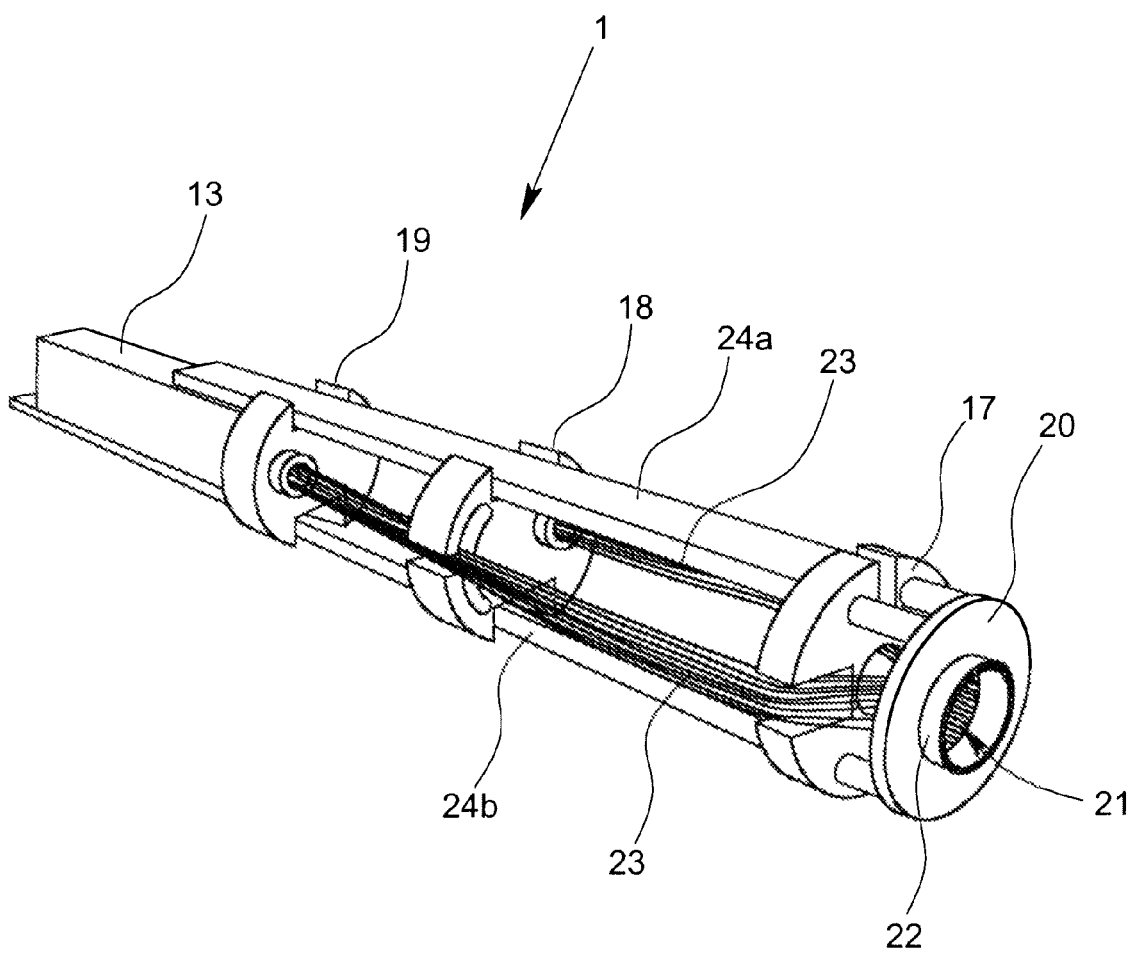

In addition to the first holding device 17, FIGS. 5 & 6 show a second holding device 18, on which the emission receiving element 4 is arranged, wherein the optical emission filter 15 is also additionally arranged on the second holding device 18. Furthermore, the device 1 also has a third holding device 19, on which the scattering-receiving element 8 is arranged, wherein the optical scattering filter 16 is also additionally arranged on the third holding device 19. Furthermore, a fourth holding device 20 is provided in which a recess 21 is provided for unobstructed flow of the radiation of the radiation source 3, wherein a circlet or wreath 22 of support elements having optical fibers therein is arranged around the recess 21 and the optical fibers 23 receive and transmit the medium radiation. By transmitting the medium radiation via the optical fibers 23, the emission-receiving element 4 and the scattering-receiving element 8 can be arranged practically arbitrarily.

In the device 1 according to FIG. 6, however, the four holding devices 17, 18, 19, 20 are held in a holder 24a, 24b and are positioned relative to one another, wherein it is advantageous, mainly, that the first holding device 17 and the fourth holding device 20 are attached to one another in the holder 24a, 24b since the mutual alignment of these holding devices 17, 20 is required for a suitable and stable alignment of the beam paths. In the embodiment according to FIG. 6, all four holding devices 17 to 20 are aligned so as to be flush relative to one another in the holder 24a, 24b, so that, all in all, a very compact construction of the device 1 is achieved. On the end, the evaluating unit 13 can be identified.

What is claimed is:

1. A method for fluorescent spectroscopic in-line determination of the protein content of a medium containing milk, comprising the steps of:
    illuminating the medium by radiation from a radiation source;
    guiding a part of the radiation from said radiation source by a beam splitter to a reference receiving element that detects the source intensity of said radiation source;
    detecting an emission intensity of a medium radiation emitted by the medium based on fluorescence with an emission-receiving element;
    detecting a scattering intensity of the medium radiation scattered by the medium in a range of the absorption of the radiation of the radiation source caused by fluorescence with a scattering-receiving element;
    measuring the temperature of the medium;
    measuring the temperature of at least one of the receiving elements;
    compensating the respective detection of radiation by the at least one of the receiving elements for an effect of the measured temperature of the least one of the receiving elements; and
    converting the detected emission intensity, in combination with the detected scattering intensity, and in combination with a compensation for an effect of the measured temperature of the medium on the fluorescence of the medium, into a concentration value of fluorescent parts of the medium,
    wherein said radiation source, said beam splitter, and said reference receiving element are commonly arranged on a holding device such that a main receiving direction of said reference receiving element and a main direction of the radiation of said radiation source are at a 90° angle to one another, and
    wherein the main direction of radiation of the radiation source is parallel to a main receiving direction of said emission-receiving element and to a main receiving direction of said scattering-receiving element.

2. The method according to claim 1, wherein:
    the measuring the temperature of the at least one of the receiving elements comprises measuring the temperature of two of the receiving elements; and
    the compensating comprises compensating the detection of the radiation by the two receiving elements for an effect of the respective measured temperature of the two of the receiving elements.

3. The method according to claim 1, wherein the fluorescence of tryptophan is used for the determination of the protein content of the medium containing milk.

4. The method according to claim 1, wherein the radiation from the radiation source is filtered by an optical filter which is maximally permeable for the frequency range of the radiation with which the fluorescence of the medium is excitable.

5. The method according to claim 1, wherein the medium radiation is filtered before being detected by the emission-receiving element by an optical emission filter which is maximally permeable for the frequency range in which the medium radiation based on fluorescence of the medium lies.

6. The method according to claim 1, wherein the medium radiation is filtered before being detected by the scattering-receiving element by an optical scattering filter which is maximally permeable for the frequency range in which the medium has its absorption maximum caused by fluorescence of the medium.

* * * * *